United States Patent
Danish et al.

(10) Patent No.: US 8,606,740 B2
(45) Date of Patent: Dec. 10, 2013

(54) CLASSIFICATION OF SUBCORTICAL STRUCTURES

(75) Inventors: Shabbar F. Danish, Philadelphia, PA (US); Stephen Wong, Upper Gywnedd, PA (US); Gordon H. Baltuch, Philadelphia, PA (US); Jurg L. Jaggi, Haddon Heights, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 707 days.

(21) Appl. No.: 12/441,973

(22) PCT Filed: Sep. 18, 2007

(86) PCT No.: PCT/US2007/020240
§ 371 (c)(1),
(2), (4) Date: Mar. 19, 2010

(87) PCT Pub. No.: WO2008/039331
PCT Pub. Date: Apr. 3, 2008

(65) Prior Publication Data
US 2010/0191695 A1 Jul. 29, 2010

Related U.S. Application Data

(60) Provisional application No. 60/826,576, filed on Sep. 22, 2006.

(51) Int. Cl.
*G06F 9/44* (2006.01)
(52) U.S. Cl.
USPC .......................................................... 706/52
(58) Field of Classification Search
None
See application file for complete search history.

(56) References Cited

U.S. PATENT DOCUMENTS 4,408,816 A * 10/1983 Knecht .................. 439/607.41
6,594,524 B2 * 7/2003 Esteller et al. .................. 607/45

FOREIGN PATENT DOCUMENTS

WO    WO 2004/093653 A2    11/2004
WO    WO 2004093653 A2 *   11/2004

OTHER PUBLICATIONS

Pesenti, A. et al., "The subthalamic nucleus in Parkinson's disease: power spectral density analysis of neural intraoperative signals," Neurol Sci., Feb. 2004, 24(6), 367-374.
Chen, C.C. et al., "Intra-operative recordings of local field potentials can help localize the subthalamic nucleus in Parkinson's disease surgery," Exp. Neurol., 2006, 198, 214-2.
Gironell, A. et al., "Usefulness of an intraoperative electrophysiological navigator system for subthalamic nucleus surgery in Parkinson's disease," Stereotact Funct Neurosurg, 2005, 83(2-3), 101-107.

* cited by examiner

*Primary Examiner* — David R Vincent
*Assistant Examiner* — Paulinho E Smith
(74) *Attorney, Agent, or Firm* — Woodcock Washburn, LLP

(57) ABSTRACT

Subcortical neural structures are classified during a microelectrode recording (MER) procedure. As the electrode traverses subcortical structures toward a target neural structure, neural activity is analyzed. The neural activity is converted to electrical signals. Features pertaining to characteristics of the neural activity are extracted from the electrical signals. The features are synergistically combined using fuzzy clustering logic, for example. In an example embodiment, the combined results are provided in a form of a color coded map indicating the different structural regions traversed. Observation of the map provides an objective indication of the demarcations of the various structural regions traversed and an objective technique for classifying the structural regions.

53 Claims, 12 Drawing Sheets

| Vehicle | Top speed [km/h] | Colour | Air resistance | Weight [kg] |
|---|---|---|---|---|
| V1 | 220 | red | 0.30 | 1300 |
| V2 | 230 | black | 0.32 | 1400 |
| V3 | 260 | red | 0.29 | 1500 |
| V4 | 140 | grey | 0.35 | 800 |
| V5 | 155 | blue | 0.33 | 950 |
| V6 | 130 | white | 0.40 | 600 |
| V7 | 100 | black | 0.50 | 3000 |
| V8 | 105 | red | 0.60 | 2500 |
| V9 | 110 | grey | 0.55 | 3500 |

CLASSIFICATION OF SUBCORTICAL STRUCTURES

CROSS-REFERENCE TO RELATED APPLICATIONS

This application is the National Stage of International Application No. PCT/US2007/020240, filed Sep. 18, 2007, which claims the benefit of U.S. Provisional Application No. 60/826,576 filed Sep. 22, 2006, the disclosure of which is incorporated herein by reference in its entirety.

TECHNICAL FIELD

The technical field generally relates to surgical techniques and more specifically relates to classification of anatomical regions during surgery.

BACKGROUND

Classifying a specific portion of an anatomical structure is often a critical component of a surgical procedure. For example, treatment of a variety of neurological disorders involves implanting a neurostimulator, or the like, into the brain of a patient. This procedure, referred to as deep brain stimulation (DBS) is an effective surgical treatment for neurological disorders such as Parkinson's disease, for example. DBS involves surgically implanting a neurostimulator for electrically stimulating a target neural structure within the brain.

Current techniques for locating and classifying a target neural structure include a process known as microelectrode recording (MER). MER is performed during surgery, just prior to implantation of the neurostimulator. During MER, an electrode is inserted through a small opening in the skull and encounters several different neural structures before reaching the target neural structure. While traversing the brain toward the target neural structure, the electrode transduces neural activity into an acoustic signal. The acoustic signal is monitored to determine when the target neural structure has been reached.

A problem with this MER technique is that it is inexact and subject to variable interpretation. Different personnel listening to the audio signal can determine that the target structure has been reached at different times. Another problem is that specifically trained personnel are typically required to interpret the audio signal. Further, the technique is affected by uncontrollable factors in the operating room, such as the quality of the microelectrode, recording cables, and the audio equipment.

SUMMARY

As an electrode traverses a brain toward a target neural structure, neural activity is analyzed to classify structural regions. Features pertaining to characteristics of the neural activity are extracted. The features are synergistically combined. In an example embodiment, the combined result is provided in a form of a color coded map indicating the different structural regions traversed. Observation of the map provides an objective indication of the demarcations of the various structural regions traversed and an objective technique for classifying the structural regions (e.g., locating subcortical structures along the microelectrode track).

BRIEF DESCRIPTION OF THE DRAWINGS

The foregoing summary, as well as the following detailed description, is better understood when read in conjunction with the appended drawings.

FIG. 9 depicts an example application of fuzzy clustering to apparently disparate variables.

DETAILED DESCRIPTION OF ILLUSTRATIVE EMBODIMENTS

In an example embodiment, subcortical structures, such as the thalamus, the zona incerta, the subthalamic nucleus (STN), a quiet zone (corresponding to white matter tracts located between the STN and the substantia nigra), and the substantia nigra (SN), are classified during a microelectrode recording (MER) procedure. The MER electrode traverses subcortical structures toward a target neural structure, such as the subthalamic nucleus. Neural activity sensed and captured by the microelectrode during the traversal is analyzed to classify structural regions. Classification comprises identifying the various deep brain nuclei and areas. Features pertaining to characteristics of the neural activity are extracted. Various feature sets are generated and the feature sets are synergistically combined. The results of the combination are provided visually. In an example embodiment, the combined results are provided in a form of a color coded map indicating the different structural regions traversed. Observation of the map provides an objective indication of the demarcations of the various structural regions traversed and an objective technique for classifying the structural regions.

Classification of subcortical structures is described herein as applied to deep brain stimulation (DBS) for the treatment of Parkinson's disease. It is to be understood that this application is exemplary and classification of subcortical structures not to be limited thereto.

Figure 1:
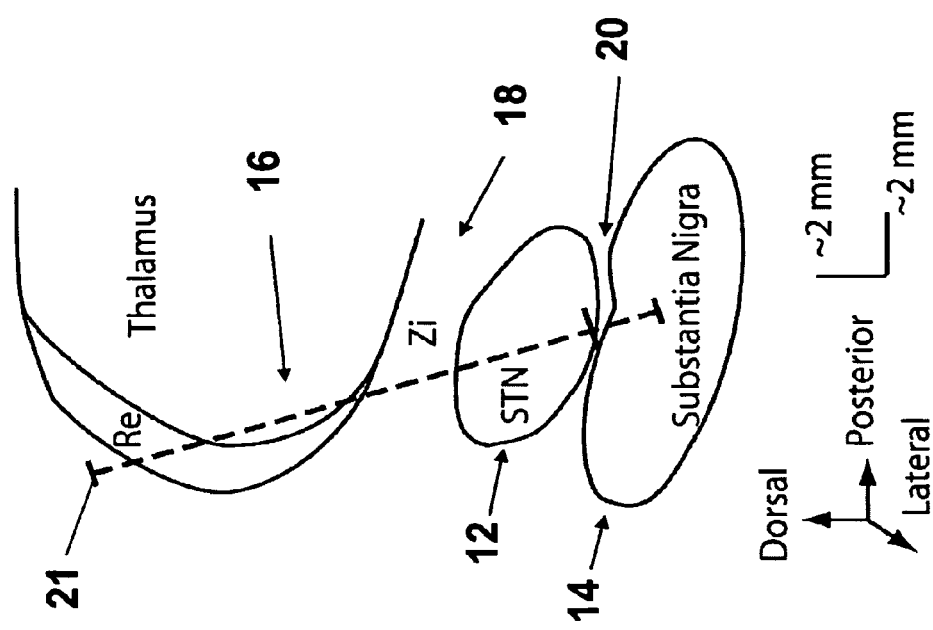
FIG. 1 is a diagram of an example microelectrode track illustrating subcortical structures encountered during targeting of the subthalamic nucleus.

FIG. 1 is diagram of an example microelectrode track illustrating subcortical structures encountered during targeting of the subthalamic nucleus. DBS is a surgical treatment for Parkinson's disease. DBS is known to provide relief from incapacitating tremors and muscle rigidity. DBS employs the implantation of a stimulating electrode into the target neural structure. Currently, the most widely targeted structure is the subthalamic nucleus (STN) 12. The efficacy of DBS is contingent upon the accurate implantation of stimulating electrodes within the target structure, such as the subthalamic nucleus 12. Several methods are known for determining the electrode trajectory 21, including preoperative magnetic resonance imaging, MRI, and computerized axial tomography, (CAT scan). Microelectrode recording (MER) can be performed during surgery, just prior to final implantation of the stimulating electrode. The electrode will encounter several different structures as depicted in FIG. 1. These structures include the thalamus 16, the zona incerta 18, the subthalamic nucleus (STN) 12, the substantia nigra (SN) 14, and a quiet zone 20 corresponding to white matter tracts located between the STN 12 and the SN 14. To perform DBS, a surgical team chooses the trajectory 21 to the target neural structure based on a number of factors. This requires denoting the entry and exit points of the target structure.

Historically, surgical teams rely on trained and experienced neurophysiologists to identify, intuitively, the appropriate target site. This method involves qualitative descriptions of regions along the microelectrode track in terms of what "sounds right." Typically, the neurophysiology team listens to changes as they happen, rather than looking at the trace in its entirety.

Figure 2:
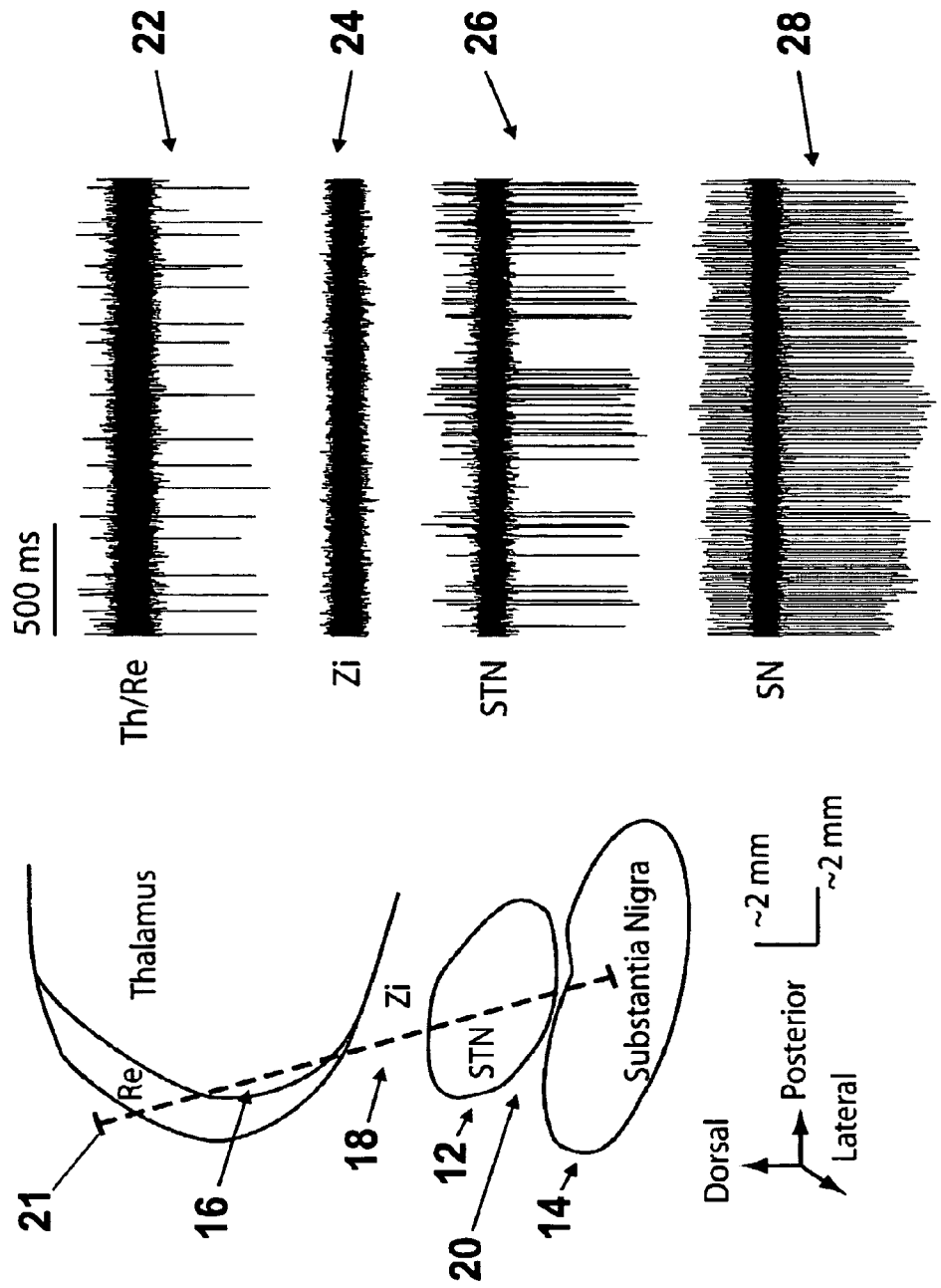
FIG. 2 is a diagram depicting example microrecording segments from the structures encountered along the microelectrode track.

FIG. 2 is a diagram showing example microrecording segments from the structures encountered along the microelectrode track. Each subcortical structure is identifiable by a respective neural signature. A microrecording representation 22 of neural activity sensed in the thalamus is shown in FIG. 2. Thalamic cells are described as bursting in nature, in a regular fashion, and in a sparse manner. A microrecording representation 26 of neural activity sensed in the subthalamic nucleus is shown in FIG. 2. The subthalamic nucleus is described by having an increase in neural noise, increased number of neuronal spikes, and a highly irregular spiking activity. A microrecording representation 28 of neural activity sensed in the substantia nigra is shown in FIG. 2. The substantia nigra is described as having a regular spiking pattern coupled with a characteristic low-frequency oscillatory pattern. Also shown in FIG. 2 is a microrecording representation 24 of neural activity sensed in the zona incerta.

In an example embodiment of the classification of subcortical structures, a visual representation is generated of the audible characteristics along the microelectrode track. Qualitative features traditionally described according to neurophysiology are transformed into visually represented features. This provides a visual representation in addition to the audible representation of the various subcortical structures as they are traversed.

Figure 3:
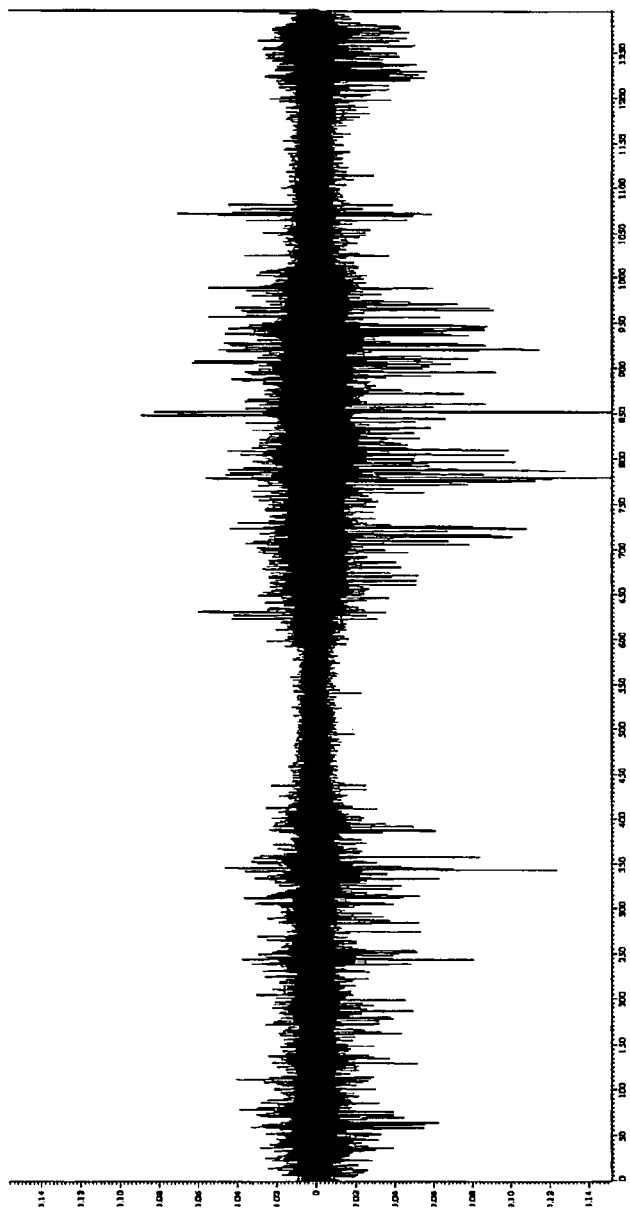
FIG. 3 is a diagram of an example recording trace from an entire MER track.
Figure 4:
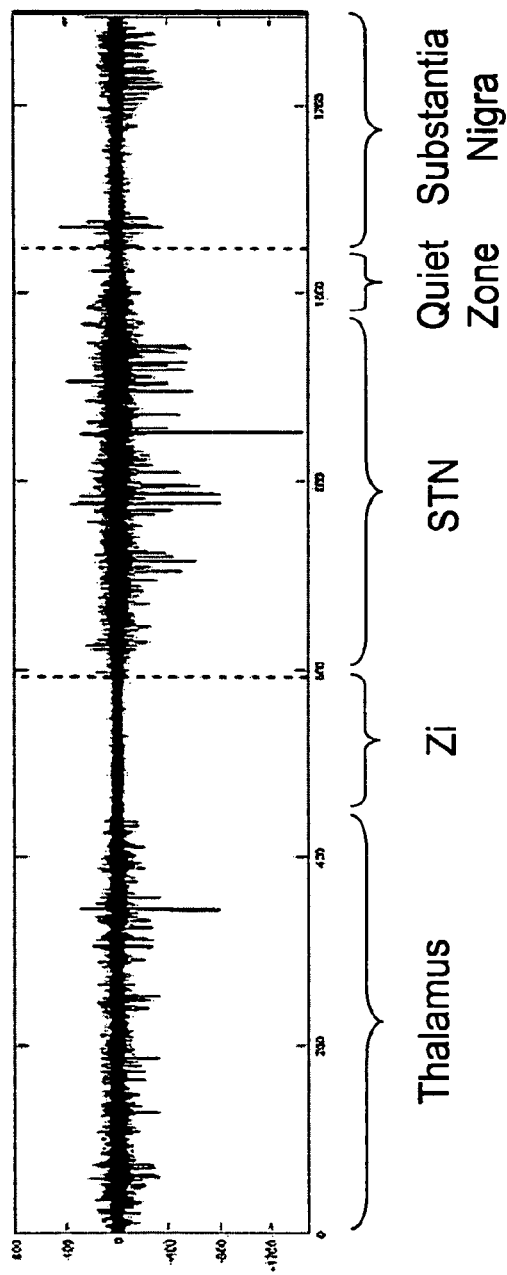
FIG. 4 is a diagram of another example recording trace from an entire MER track showing the regions of the thalamus, the zona incerta (Zi), the subthalamic nucleus (STN), the substantia nigra, the quiet zone corresponding to white matter tracts located between the STN, and the substantia nigra.

FIG. 3 is a diagram of an example recording trace from an entire MER track. Note that it is difficult to classify the various subcortical structures that are represented by the trace. FIG. 4 is a diagram of another example recording trace from an entire MER track showing the regions of the thalamus, the zona incerta (Zi), the subthalamic nucleus (STN), the substantia nigra, the quiet zone corresponding to white matter tracts located between the STN, and the substantia nigra.

A spike represents an amplitude that is detectable above the background (e.g., noise background), and has consistent morphological characteristics. In an example embodiment, a spike comprises a defined waveform representation of the amplitude. In an example embodiment, spikes are registered as negative deflections from the background. It is to be understood that representing spikes as negative deflections is exemplary and not limited thereto. When measuring local field potentials with an electrode around cell soma, there measured potentials typically have a stereotyped polarity when the cell fires. During an action potential, ions flow through the cell membrane. For example a sodium ion, $Na^+$, moves into the cell, and a potassium ion, $K^+$, moves out of the cell, and the net polarity of the cell depolarizes, resulting in an extracellular environment near the cell to be more negative at the peak of the action potential, than at baseline. This local environment is measured against an electrical reference, resulting in changes in voltage. In various embodiments, the change in voltage with respect to the reference can be positive or negative. Candidate spikes are identified as negative deflections which are larger in amplitude than a predetermined amplitude value, such as an adaptive noise threshold, for example. In an example embodiment, this adaptive threshold is set to 1.5 times the amplitude which is greater than 98% of the points in a window in the direction of the predetermined spike polarity.

Once candidate spikes are identified, they are run through various morphological rules to separate out artifacts. An example candidate spike has a width, at the zero point, of approximately 3 milliseconds. The zero point refers to the point at which the spike crosses the mean value of the data epoch. In example embodiments, the zero point can be measured before or after preprocessing, such as bandpass filtering (e.g., 500-8000 Hz), or the like. In example embodiments, deflections having a zero crossing width greater than 0.6 milliseconds are rejected. In another example embodiment, a 0.2 millisecond moving average is applied to smooth the data prior to applying the morphology rejection logic.

Other criteria apply to the spike height from peak to trough. For example, other morphological criteria, in addition to the width at the zero point of less than or equal to a predetermined value (e.g., 0.6 milliseconds) include 1) absolute value of the amplitudes of the peaks or valleys in the flanking 2 milliseconds being less than 0.9 times the zero-to-peak height of the candidate spike, and 2) trough-to-peak height of the candidate spike being greater than or equal to the adaptive threshold. The troughs are defined as the maximum values the smoothed spike reaches on either side of peak. The two criteria indicate that a spike 1) is the highest local deflection and 2) sticks out of the immediate background. In an example embodiment, a candidate spike has a slower tail end, as compared to artifact, non-candidate, spikes, as the neuron hyperpolarizes after an action potential.

Figure 5:
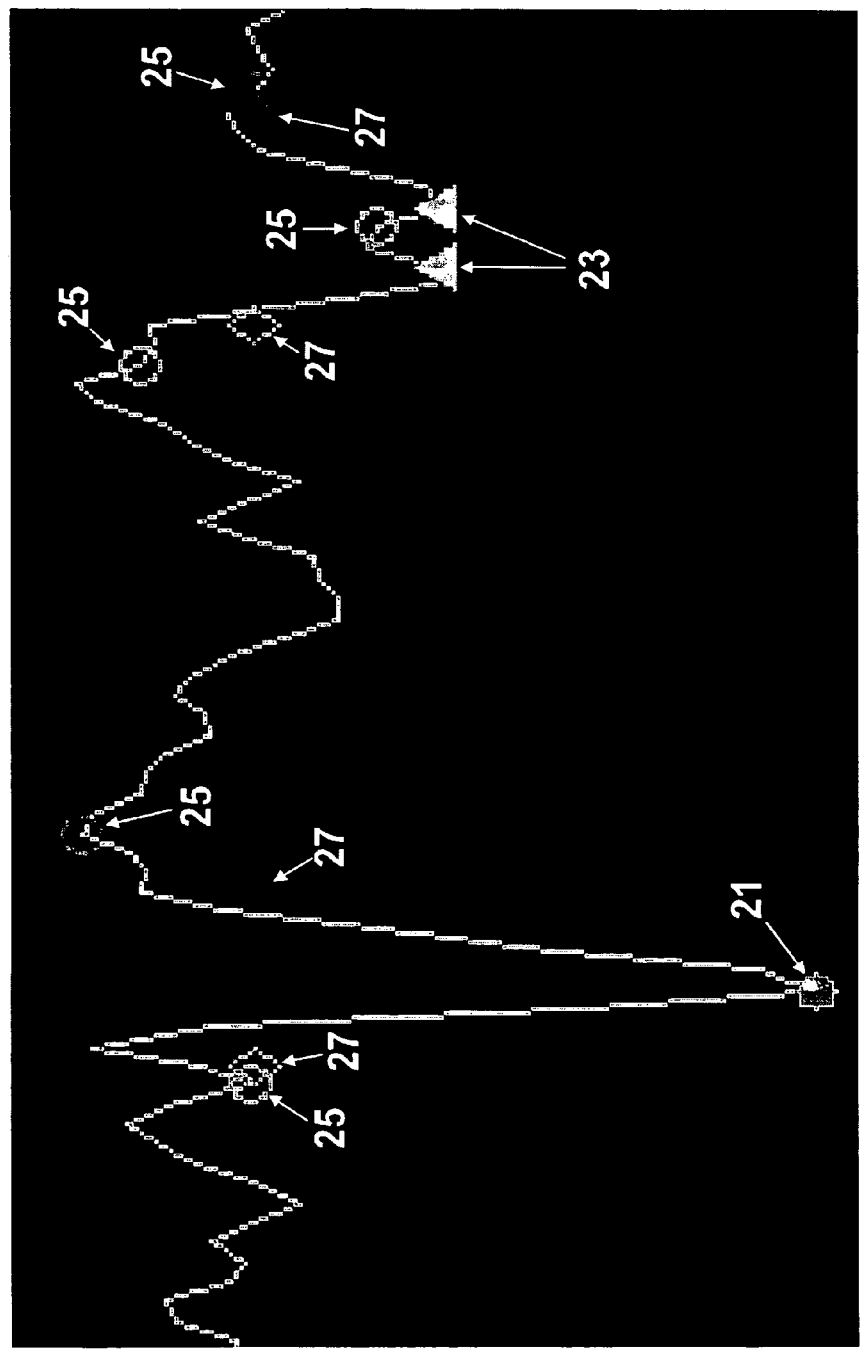
FIG. 5 is an illustrative plot of example spikes.

FIG. 5 depicts example spikes. Point 21 indicates the peak of an accepted candidate spike. Points 23 indicate peaks of rejected spikes. The spikes represented by points 23 were based on criteria (1) above, i.e., the absolute value of the amplitudes of the peaks or valleys in the flanking 2 milliseconds is less than 0.9 times the zero-to-peak height of the candidate spike. Circled points 25 represent smoothed trough points. Points 27 indicated by diamonds, represent smoothed zero points.

Figure 6:
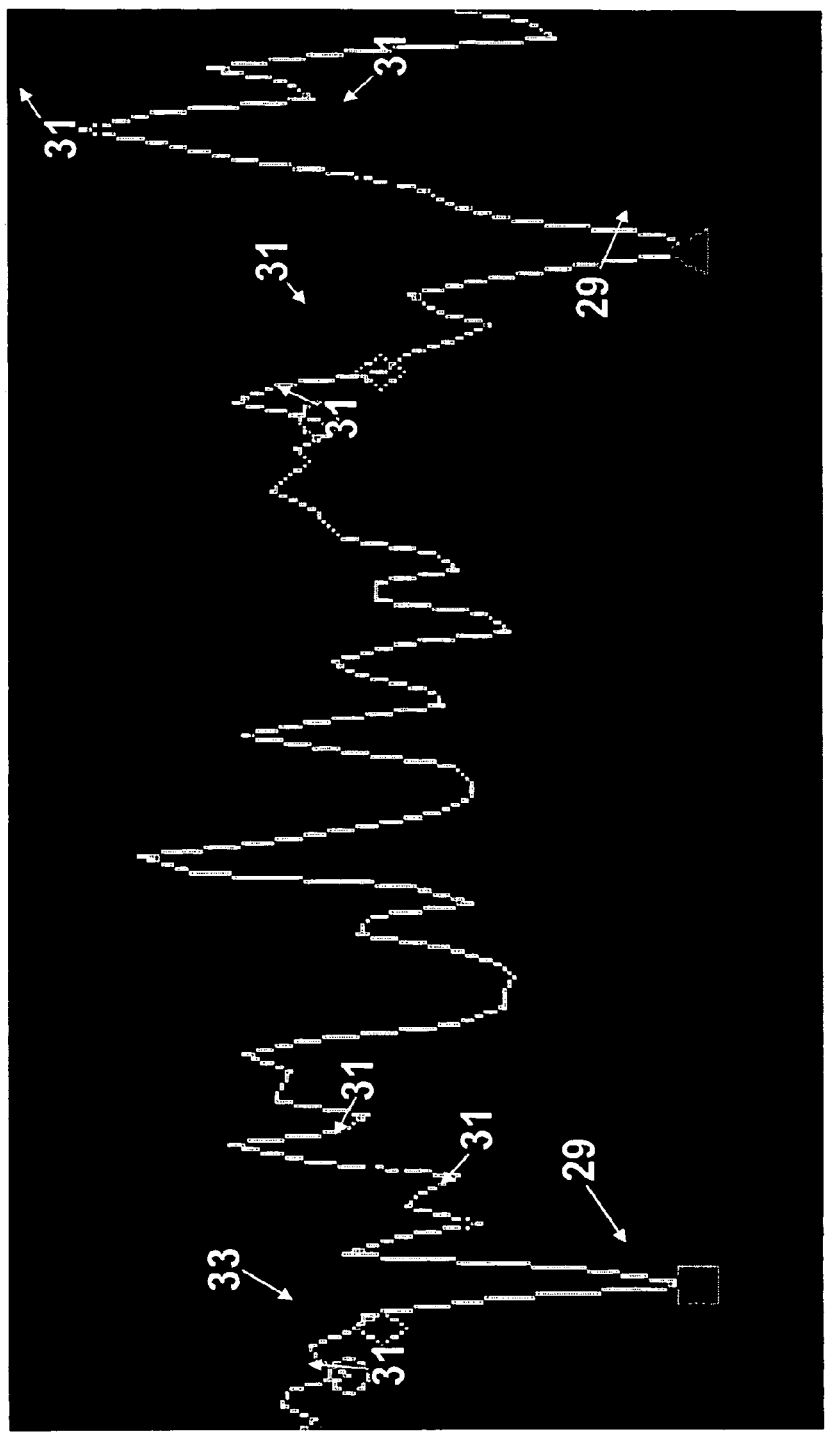
FIG. 6 is an illustrative plot of example rejected spikes.

FIG. 6 depicts example rejected spikes. Points 29 represent peaks of spikes rejected based on criteria (2) above i.e., the trough-to-peak height of the candidate spike is greater than or equal to the adaptive threshold. Points 31 (circles) represent smoothed trough points and points 33 (diamonds) represent smoothed zero points.

In an example embodiment, the time interval over which the spikes are counted (e.g., integration time) is four seconds. In an example embodiment, a four second window with a 2 second advance is utilized such that there is 50% overlap between successive windows. It is to be understood, however that any appropriate time interval can be used, and that any appropriate overlap (e.g., including zero overlap) can be used. Further, all the points, or feature vectors (described in more detail below), are calculated for each 4-second window of the microelectrode recording track (with 2-second advances). This constitutes the feature space for that recording. Because some of the features contain ratios, there is a possibility of aberrantly high numbers when the denominator of these features is low. Accordingly, in an example embodiment, the data is normalized to eliminate outliers. An example outlier is a value greater than 3 standard deviations from the mean. Outlier removal is repeated until there are no remaining outliers. The remaining data points are divided into 100 bins that are evenly distributed throughout the range of the data, and if any of the extreme bins of the histogram contain fewer than 0.5% of the data, that data is also eliminated. The remaining data are normalized to the [0,1] interval.

A point in a multidimensional feature space is defined for each 4-second window. For each window, the various spike-dependent feature values are calculated, resulting in an n-dimensional feature vector (corresponding to the coordinates of the point in the n-dimensional feature space). N is the total number of features included in the fuzzy clustering algorithm. All points, or feature vectors, are calculated for each 4-second window of the microelectrode recording track (with 2-second advances). This constitutes the feature space for that recording.

Figure 7:
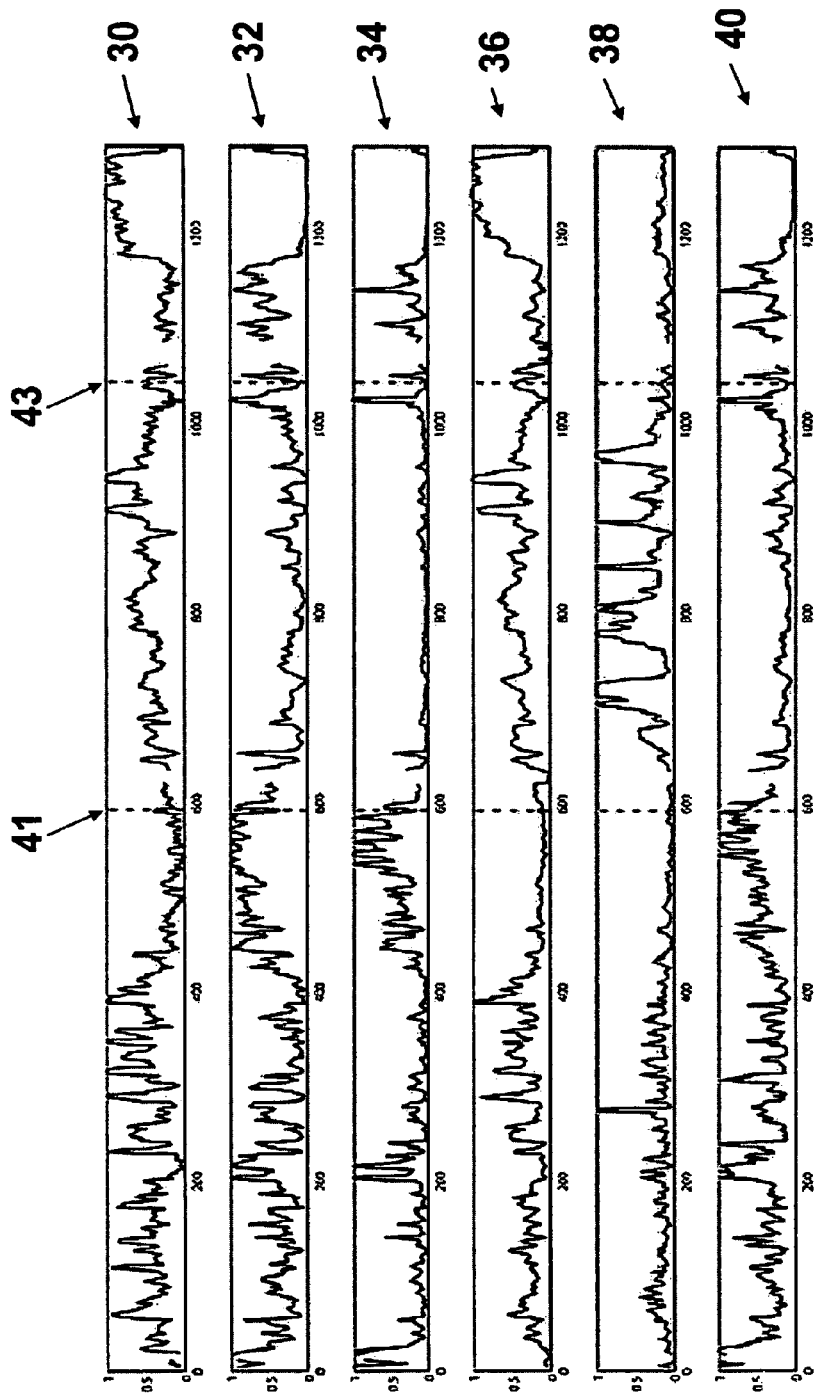
FIG. 7 is a depiction of spike-dependent features extracted from the MER trace depicted in FIG. 4.

FIG. 7 illustrates representations of spike-dependent features extracted from the MER trace depicted in FIG. 4. Each row represents an independent calculation of extracted features from the neural activity sensed along the microelectrode recording track. Each feature is plotted with respect to time.

The plots of FIG. 7 depict the normalized performance of six spike-dependent features, applied to the filtered microelectrode recording data depicted in FIG. 4. STN boundaries, as designated intraoperatively by the "gold standard" clinical neurophysiologist, are indicated by the dotted lines 41, 43. The "gold standard" represents any appropriate predetermined standard, such as determined by a clinical neurophysiologist or the like. The x-axis is time in seconds. Blanks along the feature traces indicate periods where there were not enough spikes to calculate a respective feature. Note that there is some separation of STN from its surrounding regions, but each trace, if thresholded, will exhibit false positives and false negatives.

As depicted in FIG. 7, plot 30 represents a spike dependent feature wherein is calculated the number of insterspike intervals (ISI) less than 10 ms divided by the number greater than 10 ms. Plot 32 represents a spike dependent feature wherein is calculated the number of ISI greater than 50 ms, divided by the number of ISI less than 50 ms. Plot 34 represents a spike dependent feature wherein is calculated the cumulative time of ISI greater than 50 ms divided by the cumulative time of ISI less than 50 ms. Plot 36 represents a spike dependent feature wherein is calculated the number of detected spikes. Plot 38 represents a spike dependent feature wherein is calculated the 80% trimmed mean of the absolute value of the difference between consecutive spike amplitudes, divided by the amplitude of the point which is greater than 98% of the other points. Plot 40 represents a spike dependent feature wherein is calculated the standard deviation of the ISI.

Figure 8:
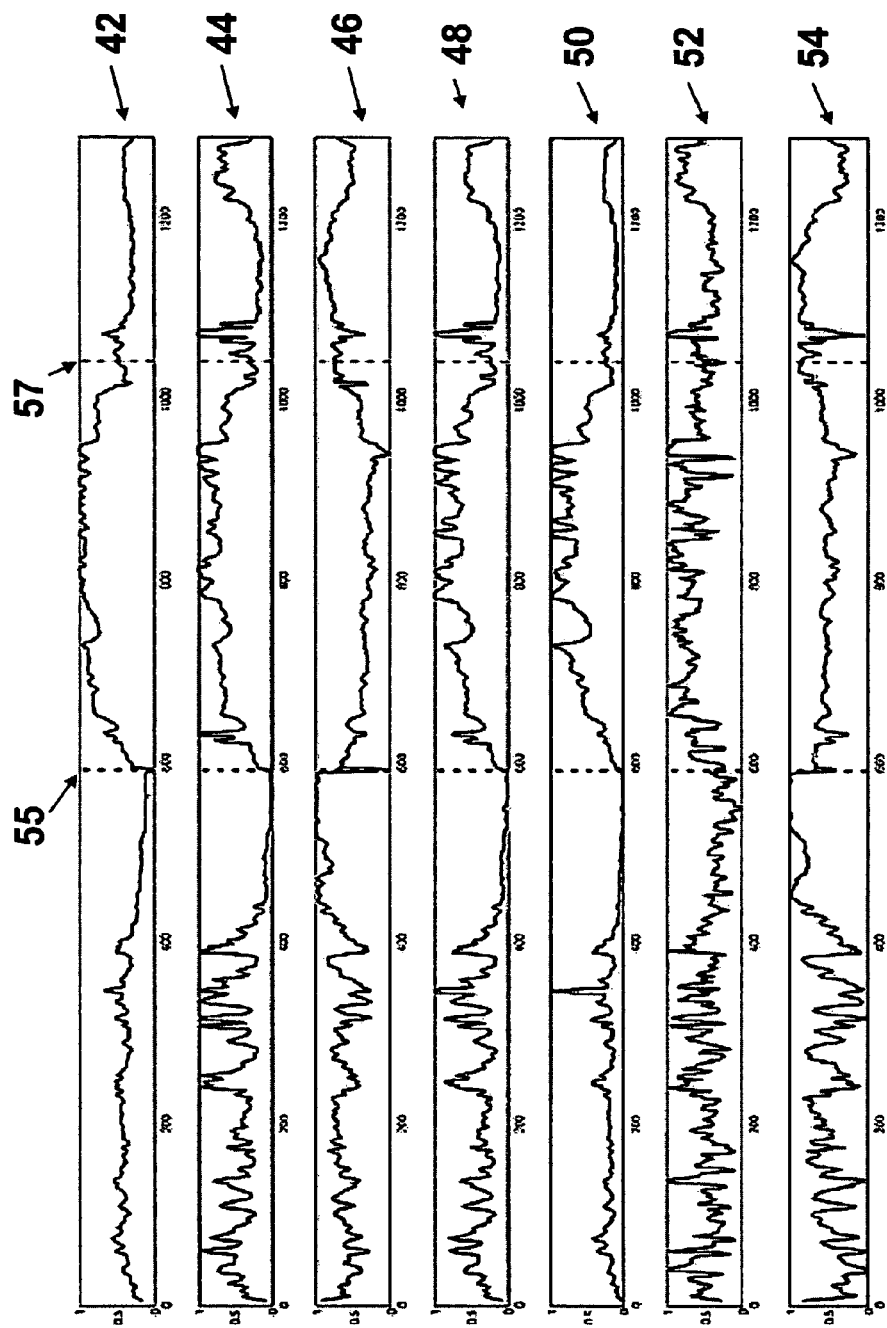
FIG. 8 is depiction of spike-independent features from the MER trace depicted in FIG. 4.

FIG. 8 illustrates representations of spike-independent features extracted from the MER trace depicted in FIG. 4. Each row represents an independent calculation of extracted features from the neural activity sensed along the microelectrode recording track. Each feature is plotted with respect to time. Plot 42 represents a spike dependent feature wherein is calculated the sum of the absolute difference between consecutive points. Plot 44 represents a spike dependent feature wherein is calculated the amplitude of the point which is greater than 98% of the other points. Plot 46 represents a spike dependent feature wherein is calculated the number of positive peaks. Plot 48 represents a spike dependent feature wherein is calculated the square root of the sum of the squared points divided by the number of points. Plot 50 represents a spike dependent feature wherein is calculated the sum of the squared points, minus the previous point multiplied by the next point. Plot 52 represents a spike dependent feature wherein is calculated the variance of the amplitudes of the data points divided by the range. Plot 54 represents a spike dependent feature wherein is calculated the number of zero crossings in the data.

FIG. 8 depicts the normalized performance of the spike-independent features described above, upon the filtered microelectrode recording data provided in FIG. 4. STN boundaries, as designated intraoperatively by the "gold standard" clinical neurophysiologist, are indicated by the dotted lines 55, 57. The x-axis is time in seconds. Note that there is some separation of STN from its surrounding regions, but each trace, if thresholded, will exhibit false positives and false negatives.

Figure 10:
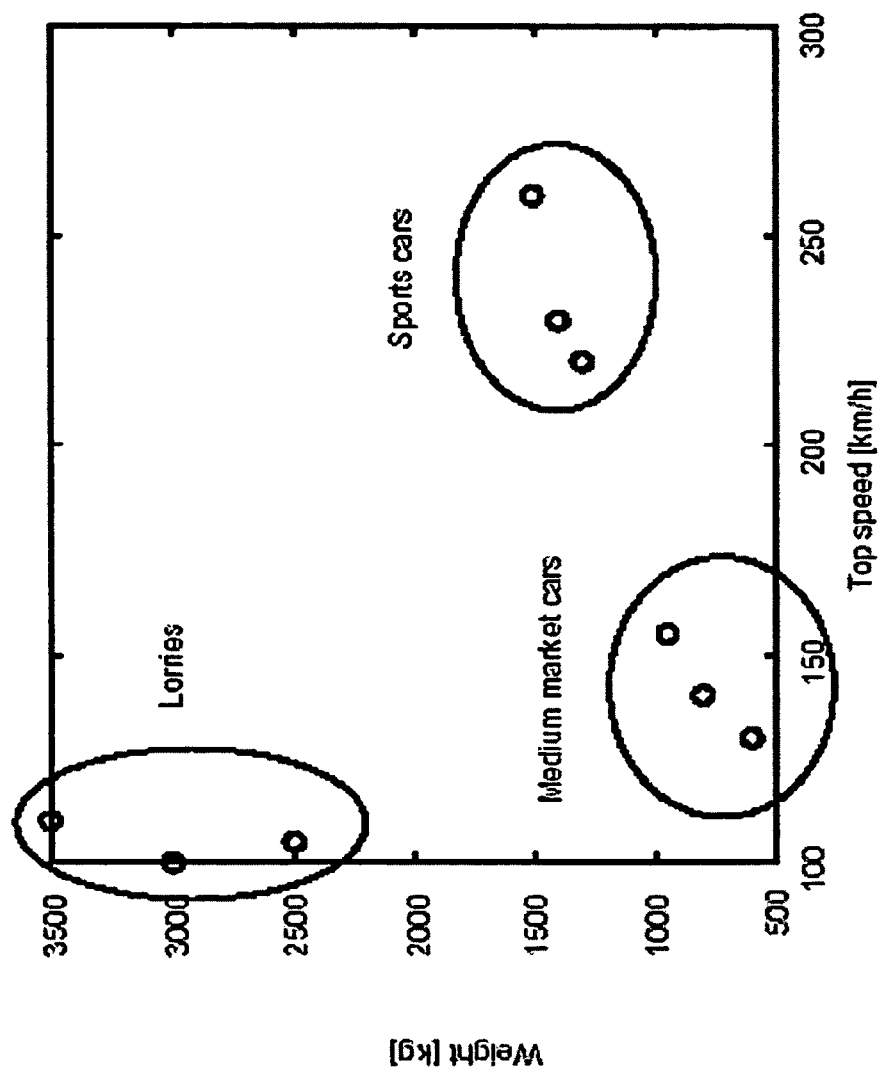
FIG. 10 depicts plotted clusters of points representing weight and speed.

The extracted features are synergistically combined and provided, in an example embodiment, as a color coded visual representation. In an example embodiment, the feature sets are combined in accordance with fuzzy clustering. Fuzzy clustering is known to allow one to find data points which exhibit common characteristics. This can enable accurate classification of the data, such as data sets in which two-dimensional relationships are not readily apparent, or present. For data sets in which a single characteristic does not provide adequate characterization, fuzzy clustering utilizes multiple dimensions to allow for more accurate classification. For example, FIG. 9 shows a table comprising vehicles and respective top speeds, colors, air resistances, and weights. For the sake of this example, three types of vehicles are defined: sport cars, medium market cars, and lorries. The three types of vehicles are defined by weight and speed. Observing the table in FIG. 9, it would be difficult to create three classifications using only two variables. However, if both variables, weight and speed, are plotted as points on a graph as depicted in FIG. 10, clusters are observed. The points "cluster" on a two-dimensional plot. These clusters can be used to define relationships that were not previously readily observable.

In an example embodiment of the classification of subcortical structures, each feature is considered to be a dimension, or mathematical equation, and occupies its own dimension. In an example embodiment, approximately 12-15 features, or dimensions, are employed in fuzzy clustering. In an example embodiment, five regions are generated corresponding to the thalamus, zona incerta, subthalamic nucleus, the white matter between the subthalamic nucleus, and substantia nigra, using the features described above.

Figure 11:
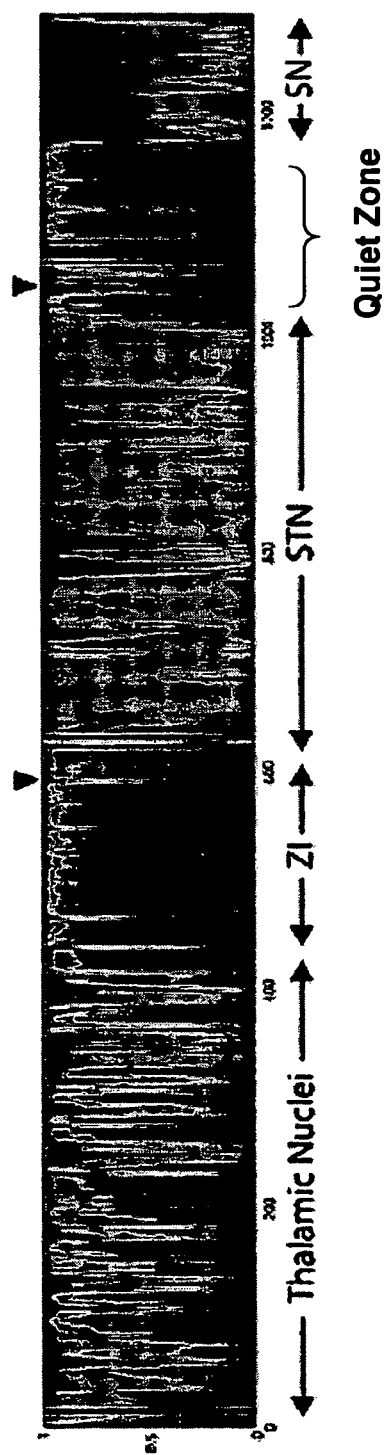
FIG. 11 is an illustration of a visual map of the microelectrode track after application of fuzzy clustering to the extracted features.

FIG. 11 is a depiction of a visual map of the microelectrode track after application of fuzzy clustering to the extracted features. The x-axis time represents time and the y-axis represents the relative proportion of each of the clusters. In an example embodiment the map depicted in FIG. 11 is color coded to facilitate the classification of structural regions. As event in FIG. 11, five separate regions can be differentiated (classified). The third region represents the subthalamic nucleus, made up of light and dark blue. Because of the clear demarcation between regions, entry and exit points of each of the structural regions can denoted from this visual map. The individual colors in this visual map are analogous to a respective cluster. Each color represents a different relationship within the data set. In an example color scheme, the colors vary smoothly from a cool blue color to a hot red color. Colors are assigned to clusters such that clusters with high spiking/background noise activity (e.g., STN) tend to be more red, whereas regions of low spiking/background noise activity tend to be more blue. Accordingly a user can determine which blob is the STN by first noting that it should be red (due to the high spiking/background noise activity), and then looking at the transitions. In a typical example embodiment, the STN is a region of red surrounded by regions of blue (because it is surrounded by regions of low spiking/background noise activity), at the expected depths.

In this example embodiment, 25 clusters are generated (which make for a relatively smooth gradation of color from blue to red in 25 steps), and each cluster is assigned a progressively "hotter" color along a single direction. Because fuzzy clustering is used, each data point has "membership" in all clusters, which is in direct (but nonlinear) relation with the distance of the data point to each cluster. Thus, a data point has all colors, but the amount of each color varies. The amount of each color, and hence membership within a cluster, is represented by a stacked bar of colors that sum to 1, with the height of each color proportional to membership.

In this example embodiment, the default direction used is the direction of higher spike count because it is robust to noise (the robustness is expected because it is a feature that has built-in high-level morphologic criteria to exclude artifact). Therefore, the deepest red colors are assigned to the clusters that have highest spike counts, and conversely, a feature point that has a high spike count value have a mostly red stacked color bar. In addition to the STN, other structures that contain spiking neurons (e.g., thalamus, substantia nigra) also show up red, but the user can differentiate them from STN because they occur at different depths. In addition, thalamic spiking areas are transient, separated by regions of inactivity, and occur over a longer dorsal-ventral span.

The ability to cycle between multiple directions quickly and automatically is allowed. Colors can be ordered along any single dimension, which is nearly equivalent to examining each feature alone. As described above, because spike count is robust to noise, the default coloring scheme is along this feature direction. When relatively noise-free recording has been achieved, color can be ordered along another feature such as curve length, which happens to be sensitive to STN rather than other structures along the microelectrode track.

Color ordering is not restricted to one dimension. Cluster colors can be ordered along a direction composed of a linear combination of features. For example, two directions of interest are the first principle component direction of the normalized data, and the diagonal from the origin to the diagonally opposite point on the normalized feature space hypercube. In these directions, all of the features are designed to acquire higher values in STN versus the flanking regions, therefore it is expected that both of these directions will result in color maps which assign STN the "hottest" red color on this example color scheme. In this way, the contribution from all features is taken into account and feature fusion results.

In accordance with this example schema, one does not have to specify what STN will look like in each particular case. Because of adaptive thresholding, normalization, and color assignments along good heuristics, inevitably STN will be assigned a red color and flanking regions will be assigned a blue color, regardless of whether or not one patient's STN spikes more or less than another. This is a nearly "unsupervised" technique, in machine learning parlance. The only input the user has to provide is integrating the patterns of red and blue and the depth data together to make a call regarding STN entry; the user could provide this information without interpreting the raw electrophysiology as is done via the current "gold standard" which requires knowledge of neurophysiology and a trained ear.

Figure 12:
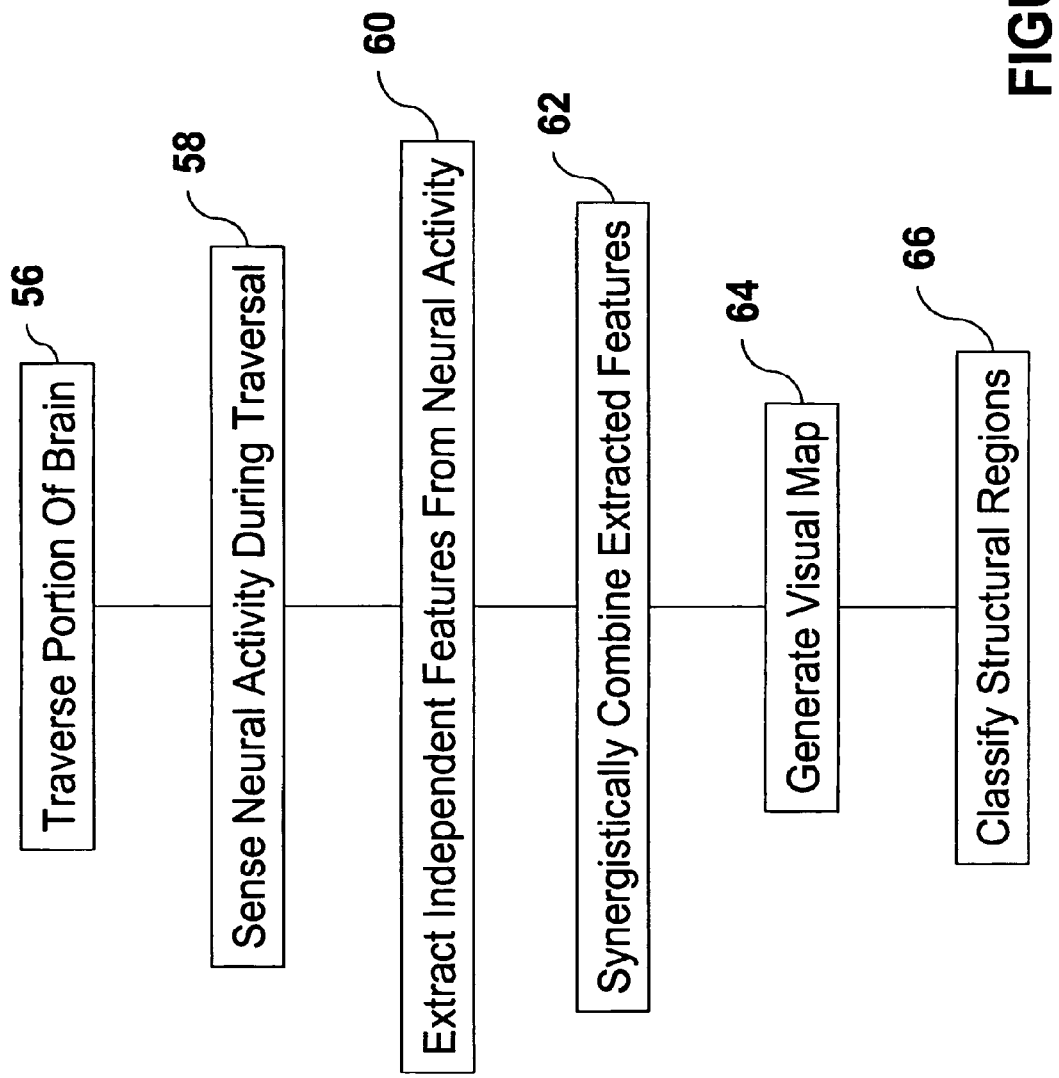
FIG. 12 is a flow diagram of an example process for classifying a region of a brain, such as subcortical structures.

FIG. 12 is a flow diagram of an example process for classifying a region of a brain, such as a subcortical structure (e.g., the subthalamic nucleus). The portion of the brain is traversed at step 56. As described above, traversal can be in accordance with a MER procedure. At step 58, neural activity is sensed during the traversal. As described above, neural activity can be sensed utilizing a microelectrode. Independent features are extracted, at step 60, from the sensed neural activity. In an example embodiment, as described above, the following spike-dependent features are determined. A feature wherein is calculated the number of insterspike intervals (ISI) less than 10 ms divided by the number greater than 10 ms, a feature wherein is calculated the number of ISI greater than 50 ms, divided by the number of ISI less than 50 ms, a feature wherein is calculated the cumulative time of ISI greater than 50 ms divided by the cumulative time of ISI less than 50 ms, a feature wherein is calculated the number of detected spikes, a feature wherein is calculated the 80% trimmed mean of the absolute value of the difference between consecutive spike amplitudes, divided by the amplitude of the point which is greater than 98% of the other points, and a feature wherein is calculated the standard deviation of the ISI. The extracted features are combined at step 62.

In an example embodiment, extracted features are synergistically combined using fuzzy clustering in accordance with the above description. In an example embodiment, spike-independent features are generated from the extracted spike-dependent features utilizing fuzzy clustering. Example spike-independent features include: a feature wherein is calculated the sum of the absolute difference between consecutive points, a feature wherein is calculated the amplitude of the point which is greater than 98% of the other points, a feature wherein is calculated the number of positive peaks, a feature wherein is calculated the square root of the sum of the squared points divided by the number of points, a feature wherein is calculated the sum of the squared points, minus the previous point multiplied by the next point, a feature wherein is calculated the variance of the amplitudes of the data points divided by the range, and a feature wherein is calculated the number of zero crossings in the data.

A visual representation of the fuzzy clustering results are provided at step 64. In an example embodiment, a color-coded map is generated. At step 66, structures are classified utilizing the visual representation (e.g., the color-coded map).

The classification of subcortical structures as described herein is spike-template independent. That is, it is not necessary to differentiate between unique neurons. Further, subcortical structures can be classified on-line, in real time, in the operating room using a standard processor, such as a personal computer, or the like. There is no dependency upon previously recorded data sets. The color-coded visual map is user friendly and offers accurate border determination. Thus, utilizing the visual color-coded map described above, the classification of subcortical structures can be determined, by a clinician or the like.

While example embodiments of the classification of subcortical structures have been described in connection with various computing devices/processor, the underlying concepts can be applied to any computing device, processor, or system capable of the classification of subcortical structures. The various techniques described herein can be implemented in connection with hardware or software or, where appropriate, with a combination of both. Thus, the methods and apparatuses for the classification of subcortical structures, or certain aspects or portions thereof, can take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for the classification of subcortical structures. In the case of program code execution on programmable computers, the computing device will generally include a processor, a storage medium readable by the processor (including volatile and non-volatile memory and/or storage elements), at least one input device, and at least one output device. The program(s) can be implemented in assembly or machine language, if desired. The language can be a compiled or interpreted language, and combined with hardware implementations.

The methods and apparatuses for the classification of subcortical structures also can be practiced via communications embodied in the form of program code that is transmitted over some transmission medium, such as over-electrical wiring or cabling, through fiber optics, or via any other form of transmission, wherein, when the program code is received and loaded into and executed by a machine, such as an EPROM, a gate array, a programmable logic device (PLD), a client computer, or the like, the machine becomes an apparatus for the classification of subcortical structures. When implemented on a general-purpose processor, the program code combines with the processor to provide a unique apparatus that operates to invoke the functionality of the classification of subcortical structures. Additionally, any storage techniques used in connection with the classification of subcortical structures can invariably be a combination of hardware and software.

While the classification of subcortical structures has been described in connection with the various embodiments of the various figures, it is to be understood that other similar embodiments can be used or modifications and additions can be made to the described embodiment for performing the same function of the classification of subcortical structures without deviating therefrom. For example, one skilled in the art will recognize that the classification of subcortical structures as described in the present application may apply to any environment, whether wired or wireless, and may be applied to any number of such devices connected via a communications network and interacting across the network. Therefore, the classification of subcortical structures should not be limited to any single embodiment, but rather should be construed in breadth and scope in accordance with the appended claims.

What is claimed:

1. A method for producing a visual functional map of a region of a brain, the method comprising:
    traversing a portion of the brain;
    sensing neural activity during the traversal;
    extracting a plurality of features from the sensed neural activity;
    combining characteristics of the extracted plurality of features; and
    providing a visual functional map of the combined characteristics of the plurality of features over time or depth.

2. The method in accordance with claim 1, further comprising classifying at least one region of the portion in accordance with the combined characteristics.

3. The method in accordance with claim 1, wherein the characteristics are combined in accordance with fuzzy clustering.

4. The method in accordance with claim 1, further comprising sensing the neural activity via a microelectrode recorder.

5. The method in accordance with claim 1, wherein the portion of the brain comprises a subcortical structure of the brain.

6. The method in accordance with claim 5, wherein the region comprises a thalamus.

7. The method in accordance with claim 5, wherein the region comprises a zona incerta.

8. The method in accordance with claim 5, wherein the region comprises a subthalamic nucleus.

9. The method in accordance with claim 5, wherein the region comprises a substantia nigra.

10. The method in accordance with claim 5, wherein the subcortical structure comprises a plurality of regions comprising:
    a subthalamic nucleus of the portion;
    a substantia nigra of the portion; and
    a white matter tract located between the subthalamic nucleus and the substantia nigra.

11. The method in accordance with claim 1, wherein one of the plurality of features comprises;
    a number of time intervals less than a predetermined value divided by a number of time intervals greater than the predetermined value, wherein:
        a time interval comprises an amount of time elapsing between two occurrences of an abrupt increase in amplitude of a representation of the sensed neural activity.

12. The method in accordance with claim 11, wherein the predetermined value is ten milliseconds.

13. The method in accordance with claim 11, wherein the one of the plurality of features is determined from neural activity sensed for a predetermined period of time.

14. The method in accordance with claim 13, wherein the predetermined period of time is four seconds.

15. The method in accordance with claim 1, wherein one of the plurality of features comprises:
    a number of time intervals greater than a predetermined value divided by a number of time intervals less than the predetermined value, wherein:
        a time interval comprises an amount of time elapsing between two occurrences of an abrupt increase in amplitude of a representation of the sensed neural activity.

16. The method in accordance with claim 15, wherein the predetermined value is fifty milliseconds.

17. The method in accordance with claim 15, wherein the one of the plurality of features is determined from neural activity sensed for a predetermined period of time.

18. The method in accordance with claim 17, wherein the predetermined period of time is four seconds.

19. The method in accordance with claim 1, wherein one of the plurality of features comprises:
    a cumulative amount of time that a number of time intervals are greater than a predetermined value divided by a cumulative amount of time that a number of time intervals are less than the predetermined value, wherein:
        a time interval comprises an amount of time elapsing between two occurrences of an abrupt increase in amplitude of a representation of the sensed neural activity.

20. The method in accordance with claim 19, wherein the predetermined value is fifty milliseconds.

21. The method in accordance with claim 19, wherein the one of the plurality of features is determined from neural activity sensed for a predetermined period of time.

22. The method in accordance with claim 21, wherein the predetermined period of time is four seconds.

23. The method in accordance with claim 1, wherein one of the plurality of features comprises a number of abrupt increases in amplitude of a representation of the sensed neural activity.

24. The method in accordance with claim 23, wherein the one of the plurality of features is determined from neural activity sensed for a predetermined period of time.

25. The method in accordance with claim 24, wherein the predetermined period of time is four seconds.

26. The method in accordance with claim 1, wherein one of the plurality of features comprises:
   detecting a number of abrupt increases in amplitude of a representation of the sensed neural activity;
   determining an amplitude for each of two temporally consecutive detected abrupt increases in amplitude of a representation of the sensed neural activity;
   determining an absolute value of each difference between the two consecutive amplitudes;
   determining a mean value of 80% of the absolute values;
   determining a value of one of the detected abrupt increases in amplitude indicative of a 98th percentile of the detected abrupt increases in amplitude; and
   dividing the mean value of 80% of the absolute values by the value of the abrupt increases in amplitude indicative of a $98^{th}$ percentile of the detected abrupt increases in amplitude.

27. The method in accordance with claim 26, wherein the one of the plurality of features is determined from neural activity sensed for a predetermined period of time.

28. The method in accordance with claim 27, wherein the predetermined period of time is four seconds.

29. The method in accordance with claim 1, wherein one of the plurality of features comprises:
   a standard deviation of time intervals, wherein:
      a time interval comprises an amount of time elapsing between two occurrences of an abrupt increase in amplitude of a representation of the sensed neural activity.

30. The method in accordance with claim 29, wherein the one of the plurality of features is determined from neural activity sensed for a predetermined period of time.

31. The method in accordance with claim 30, wherein the predetermined period of time is four seconds.

32. The method in accordance with claim 1, wherein one of the plurality of features comprises:
   detecting a number of abrupt increases in amplitude of a representation of the sensed neural activity;
   determining an amplitude for each of two temporally consecutive detected abrupt increases in amplitude of a representation of the sensed neural activity;
   determining an absolute value of each difference between the two consecutive amplitudes; and
   determining a sum of the absolute values.

33. The method in accordance with claim 32, wherein the one of the plurality of features is determined from neural activity sensed for a predetermined period of time.

34. The method in accordance with claim 33, wherein the predetermined period of time is four seconds.

35. The method in accordance with claim 1, wherein one of the plurality of features comprises:
   detecting a number of abrupt increases in amplitude of a representation of the sensed neural activity; and
   determining a value of one of the detected abrupt increases in amplitude indicative of a $98^{th}$ percentile of the detected abrupt increases in amplitude.

36. The method in accordance with claim 35, wherein the one of the plurality of features is determined from neural activity sensed for a predetermined period of time.

37. The method in accordance with claim 36, wherein the predetermined period of time is four seconds.

38. The method in accordance with claim 1, wherein one of the plurality of features comprises a number of positive abrupt increases in amplitude of a representation of the sensed neural activity.

39. The method in accordance with claim 38, wherein the one of the plurality of features is determined from neural activity sensed for a predetermined period of time.

40. The method in accordance with claim 39, wherein the predetermined period of time is four seconds.

41. The method in accordance with claim 1, wherein one of the plurality of features comprises:
   detecting a number of abrupt increases in amplitude of a representation of the sensed neural activity;
   determining an amplitude value for each of the detected abrupt increases in amplitude;
   squaring each amplitude value;
   determining a sum of the squared amplitude values; and
   determining a square root of the sum.

42. The method in accordance with claim 41, wherein the one of the plurality of features is determined from neural activity sensed for a predetermined period of time.

43. The method in accordance with claim 42, wherein the predetermined period of time is four seconds.

44. The method in accordance with claim 1, wherein one of the plurality of features comprises:
   detecting a number of abrupt increases in amplitude of a representation of the sensed neural activity;
   determining an amplitude value for each of the detected abrupt increases in amplitude;
   squaring each amplitude value;
   determining a sum of the squared amplitude values; and
   for each detected abrupt increase in amplitude, determining a difference between the sum minus a product of:
      a temporally previous abrupt increase in amplitude; and
      a temporally subsequent abrupt increase in amplitude.

45. The method in accordance with claim 44, wherein the one of the plurality of features is determined from neural activity sensed for a predetermined period of time.

46. The method in accordance with claim 45, wherein the predetermined period of time is four seconds.

47. The method in accordance with claim 1, wherein one of the plurality of features comprises:
   detecting a number of abrupt increases in amplitude of a representation of the sensed neural activity;
   determining an amplitude value for each of the detected abrupt increases in amplitude;
   determining a variance of the amplitude values;
   determining a difference between a maximum amplitude value and a minimum amplitude value; and
   dividing the variance by the difference.

48. The method in accordance with claim 47, wherein the one of the plurality of features is determined from neural activity sensed for a predetermined period of time.

49. The method in accordance with claim 48, wherein the predetermined period of time is four seconds.

50. The method in accordance with claim 1, wherein one of the plurality of features comprises:
   detecting a number of abrupt changes in amplitude of a representation of the sensed neural activity; and
   determining a number of times temporally consecutive detected abrupt changes traverse a zero value.

51. The method in accordance with claim 50, wherein the one of the plurality of features is determined from neural activity sensed for a predetermined period of time.

52. The method in accordance with claim 51, wherein the predetermined period of time is four seconds.

53. A computer-readable medium comprising computer-executable instructions for classifying a region of a brain, wherein the medium is not a propagating signal, the computer-executable instructions for:
   traversing a portion of the brain;
   sensing neural activity during the traversal;
   extracting a plurality of features from the sensed neural activity;
   combining characteristics of the extracted plurality of features; and
   providing a visual functional map of the combined characteristics of the plurality of features over time or depth.

\* \* \* \* \*

UNITED STATES PATENT AND TRADEMARK OFFICE
CERTIFICATE OF CORRECTION

PATENT NO. : 8,606,740 B2
APPLICATION NO. : 12/441973
DATED : December 10, 2013
INVENTOR(S) : Danish et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1152 days.

Signed and Sealed this
Twenty-second Day of September, 2015

Michelle K. Lee
*Director of the United States Patent and Trademark Office*